(12) United States Patent
Rongen et al.

(10) Patent No.: US 8,301,222 B2
(45) Date of Patent: Oct. 30, 2012

(54) DEVICE FOR MEASURING BIOMEDICAL DATA OF A TEST SUBJECT AND METHOD FOR STIMULATING THE TEST SUBJECT USING DATA PROCESSED IN REAL TIME

(75) Inventors: Heinz Rongen, Dueren (DE); Karl Ziemons, Aachen (DE); Michael Schiek, Aachen (DE); Peter Alexander Tass, Titz (DE)

(73) Assignee: Forschungszentrum Juelich GmbH, Juelich (DE)

( * ) Notice: Subject to any disclaimer, the term of this patent is extended or adjusted under 35 U.S.C. 154(b) by 805 days.

(21) Appl. No.: 12/226,289

(22) PCT Filed: Mar. 23, 2007

(86) PCT No.: PCT/DE2007/000539
§ 371 (c)(1),
(2), (4) Date: Oct. 30, 2008

(87) PCT Pub. No.: WO2007/118443
PCT Pub. Date: Oct. 25, 2007

(65) Prior Publication Data
US 2009/0069662 A1    Mar. 12, 2009

(30) Foreign Application Priority Data

Apr. 15, 2006   (DE) .......................... 10 2006 017 716

(51) Int. Cl.
*A61B 5/0476* (2006.01)
*A61B 5/055* (2006.01)
*G06F 19/00* (2011.01)

(52) U.S. Cl. ............................ 600/409; 600/504; 702/19

(58) Field of Classification Search ........................ None
See application file for complete search history.

(56) References Cited

U.S. PATENT DOCUMENTS

| | | | |
|---|---|---|---|
| 4,479,263 A | 10/1984 | Rosenfeldt et al. | |
| 4,955,388 A | 9/1990 | Silberstein | |
| 5,099,854 A | 3/1992 | Choi | |
| 5,099,856 A | 3/1992 | Killion et al. | |
| 5,331,969 A | 7/1994 | Silberstein | |
| 5,445,162 A * | 8/1995 | Ives | 600/544 |
| 5,581,387 A | 12/1996 | Cahill | |
| 2004/0073202 A1 | 4/2004 | Illich et al. | |
| 2005/0154424 A1 | 7/2005 | Tass et al. | |

FOREIGN PATENT DOCUMENTS

| | | |
|---|---|---|
| DE | 30 19 668 | 5/1980 |
| DE | 40 30 782 | 4/1992 |
| DE | 199 50 919 | 10/1999 |
| DE | 102 11 765 | 3/2002 |
| DE | 102 36 175 | 2/2004 |
| DE | 695 30 768 | 3/2004 |
| JP | 63-500434 | 2/1988 |
| JP | 2000-151011 | 5/2000 |
| WO | WO-87/00746 | 2/1987 |

OTHER PUBLICATIONS

Pozzo M et al: "Sixty-Four Channel Wearable Acquisition System for Long-Term Surface Electromyogram Recordign With Electrode Arrays" Medical and Biological Engineering and Computing, Springer, Heildelberg, DE, vol. 42, No. 4, Jul. 2004, pp. 455-466, XP001221029 ISSN: 0140-0118 p. 461-p. 465; figure 4.
Rongen H., u.a.: Real Time Data Acquisition and Online Signal Processing for Magnetoencephalography. In: 14, IEEE-NPSS Real Time Conference, 4. bis 10. Juni 2005, Seiten 495 bis 497.

* cited by examiner

*Primary Examiner* — Michael Borin
(74) *Attorney, Agent, or Firm* — Jordan and Hamburg LLP

(57) ABSTRACT

Provided is a device for measuring biomedical data from a testee, with a recording system for taking the data and a first hardware component for displaying the data. A device for electrical separation of the data is arranged in a connector line for transmitting the data from the recording system to the first hardware component for displaying the data. At least a duplication of the data for data processing purposes is thus guaranteed. The data processed in said manner are used for a method for real-time stimulation of a testee.

14 Claims, 4 Drawing Sheets

DEVICE FOR MEASURING BIOMEDICAL DATA OF A TEST SUBJECT AND METHOD FOR STIMULATING THE TEST SUBJECT USING DATA PROCESSED IN REAL TIME

BACKGROUND OF THE INVENTION

The invention relates to a device for measuring biomedical data of a test subject and to a method for stimulating the test subject using data processed in real time.

Devices, in the form of multi-channel recorders, which record an electromagnetic correlate of the neuronal activity of a test subject as a function of time, have been the state of the art for many years.

Electroencephalographs (EEG) and magnetoencephalographs (MEG) are mentioned by way of example.

These devices comprise a plurality of measurement channels. The devices are not only capable of detecting signals, but also to save and evaluate the data. The evaluation of the data is performed with the device in the offline mode, which is to say at a time at which no data is acquired from the test subject. To this end, the data acquired by the device is forwarded to a workstation, saved, and optionally further processed.

The acquisition of data sets by means of a 148-channel magnetoencephalograph and the storage, processing and visualization of these sets for 3D reconstruction of the brain is known from Rongen et al (H. Rongen, V. Hadamschek, M. Schiek (2005). *Real-Time Data Acquisition and Online Signal Processing for Magnetoencephalography*. In: Conference Proceedings of the IEEE-NPSS Real Time Conference 2005, Jun. 4-10, Stockholm, Sweden, pp 5-7). The disadvantage is that it is not possible to process and evaluate the data in real time, in line with the ongoing measurement of the data on the test subject.

SUMMARY OF THE INVENTION

It is the object of the invention to provide a device for measuring the biomedical data of a test subject, wherein the device allows recording and processing of the data in real time. Another object of the invention is to provide a method for using data processed in this way.

The object is achieved by a device according to the principal claim and a method according to the additional independent claim. Advantageous embodiments will be apparent from the claims that reference these claims.

The device comprises a measuring system for acquisition of the data and a first hardware component for recording the data. A connecting line for transmitting the data is provided between the measuring system and the first hardware component. According to the invention, a means for the electrical isolation of the data is provided on the connecting line, between the first hardware component for recording the data and the measuring system for acquisition of the data. The means for electrical isolation advantageously achieves electrical decoupling of both the test subject and the measuring system for acquisition of the data, from the remaining hardware components for recording and processing the data, these components being connected downstream. According to the Medical Devices Act and in concordance with the fundamental requirements of MDD 93/42 EEC, this is a necessity.

This prevents injury to the test subject in the event of electrical interference affecting these hardware components that are connected downstream. The measuring system for acquisition of the data is, of course, also protected from interference.

In the case of an electroencephalograph, or a magnetoencephalograph, the measuring system for acquisition of the data comprises electrodes, measuring channels, and other equipment-specific components, such as sensors and the like. These may vary, depending on the supplier of the device.

The test subject does not necessarily have to be a human. Rather, any animal, and particularly any mammal, can serve as a test subject. Of course, it is also possible to examine and/or stimulate biologically active brain and/or tissue sections of a test subject in the manner disclosed here.

The means for isolating the data advantageously ensures interference-free isolation and copying of the data in a data set into at least two identical data sets.

Interference-free isolation of the data advantageously means that the isolating process does not influence the measuring system for acquisition of the data and therefore also does not influence the acquired data.

The interference-free isolation of the data itself thus leaves both the data and the test subject completely uninfluenced.

It is possible to configure a device according to the invention having a means according to the invention so that the means isolates the data acquired by the measuring system into more than two identical data sets. In any case, the data acquired by the measuring system remains unchanged by the isolation of the data.

The connecting line between the measuring system and the first hardware component is particularly advantageously formed by an optical fiber, on which an optical fiber coupler is provided as the means according to the invention.

Instead of an optical fiber, it is possible to provide a copper line between the measuring system and the first hardware component, as the connecting line, on which an isolation amplifier is provided, as the means according to the invention.

The first hardware component is constituted, for example, by a workstation. According to the state of the art, it constantly controls the measurement process of a measuring system for acquisition of the data. For this purpose, another connecting line is provided between the first hardware component and the measuring system for acquisition of the data.

The measuring system for acquisition of the data, the first hardware component, and a connecting line between the measuring system and the first hardware component constitute the state of the art with respect to electroencephalographs (EEG) or magnetoencephalographs (MEG).

The means for electrical isolation of the data on the connecting line expands devices of this type and allows the data not only to be stored in the first hardware component, but also to be further processed in real time in a second hardware component.

Thus, in addition to recording and long-term storage in the first hardware component, the data acquired by the measuring system can also advantageously be supplied to at least one further second hardware component for processing of the data in real time.

The means for isolation of the data according to the invention is advantageously configured as a passive means.

In this way, the second hardware component for the processing and storage of the data only "listens in" to the existing data stream that is provided to the first hardware component, without actively intervening in the data stream. The second hardware component behaves passively in relation to the data stream.

The means for isolation of the data is thus provided on the connecting line extending from the measuring system for acquisition of the test subject data, so as to isolate the data stream from the measuring system for acquisition of the data with respect to two connecting lines. A line extending from the means according to the invention forwards the data stream to the first hardware component for recording of the data. At least one further data stream is forwarded to the second hardware component.

In this way, a complete, identical data set is also supplied to at least the second hardware component.

The second hardware component processes the data in real time and stores both the incoming and the processed data. It is possible that the second hardware component also controls the measuring system for acquisition of data.

Real time data processing in the second hardware component particularly advantageously enables a method for stimulating the test subject using the processed data, by returning or forwarding the processed data to the test subject in real time.

In one embodiment of the invention, the second hardware component for processing the data comprises a PCI mainboard, on which the components for real time data processing and storage of incoming and processed data are disposed. To this end, the PCI mainboard is an expansion to a computer.

For this purpose, the PCI mainboard advantageously comprises elements or components for a data acquisition and processing unit, and notably also comprises elements or components for generating feedback signals to the test subject. To this end, the PCI mainboard is provided with a powerful real-time data acquisition and processing unit. As a matter or course, the PCI mainboard further comprises additional components for storage purposes, and optionally for controlling the measuring system for acquisition of data.

The PCI mainboard of the second hardware component particularly advantageously comprises a digital signal processor (DSP), for example a Texas Instruments TMS320c6713 for processing data in real time.

In a further embodiment of the invention, the PCI mainboard of the second hardware component comprises a field programmable gate array (FPGA), for example a Virtex XCV300.

However, the second hardware component does not necessarily have to comprise a field programmable gate array (FPGA). The second hardware component only has to be powerful enough to capture the incoming data and perform the necessary calculations for generating feedback signals, in line with acquisition of data by the measuring system. The second hardware component for processing the data also comprises outputs necessary for forwarding the data, which was acquired by the measuring system and processed, to the test subject.

Using suitable algorithms, which can be stored in the digital signal processor (DSP), feedback signals are generated from the processed data for stimulating the test subject, in line with the measurement of the data by the measuring system, and fed back to the test subject via suitable connecting lines.

The PCI mainboard advantageously comprises a PCI bus interface and the necessary input and output components.

In the case of optical fibers, in addition to an optical fiber interface, these include analog and digital inputs and outputs.

As a result, this data acquisition and processing unit provides all the necessary interfaces for connecting to a measuring system for acquisition of the data such as a magnetoencephalograph, an electroencephalograph or the like.

The data is processed by means of the second hardware component using algorithms, which can be stored on the PCI mainboard in the FPGA and in the DSP. Using a third hardware component, the data, which is based on the measurement data, and is processed in the second hardware component, is forwarded in the form of feedback signals to the test subject for stimulation purposes. In a particularly advantageous embodiment, this occurs in line with the data acquisition by the measuring system and the processing of the data by the second hardware component.

Forwarding of the processed data to the test subject is time delayed by a fixed delay period or by a certain variable, known delay period, with reference to the signal detection, so that the test subject can be stimulated based on the currently acquired and processed measurement signals.

To this end, the third hardware component comprises optical stimulation goggles in a particularly advantageous embodiment.

Thus, the third hardware component for stimulation, for example, encompasses a linear control for a light source, for visual stimulation.

However, it is also possible to provide acoustic stimulation for the test subject, using the data that was acquired from the subject and processed.

To this end, the third hardware component advantageously comprises a sound source, which can be controlled in terms of volume and/or frequency by means of analog output signals from the second hardware component. The acoustic signal is supplied to the test subject via a speaker or headphones, so that the subject is again stimulated. The device according to the invention is advantageously used for interference-free expansion of existing measuring systems and devices, such as magnetoencephalographs or electroencephalographs, whereby these systems and devices are expanded to include electrical and magnetic stimulation of the test subject.

According to the invention, the devices are expanded by components capable of real time feedback. To this end, any commercially available measuring system can be expanded by the means according to the invention for the electric isolation of the acquired data and for processing of the data.

A method according to the invention for stimulating a test subject comprises the following steps:

a) test subject data is acquired by a measuring system,
b) the acquired data is electrically isolated and a copy of the data set is supplied to a real-time data processing unit,
c) the data is processed in real time,
d) the processed data is forwarded to the test subject.

The processed data in d) is forwarded to the test subject in the form of analog signals.

Steps a) to d) are repeated multiple times, for example, approximately a thousand times per second.

Using the method according to the invention, the data is transformed in a linear or non-linear manner and returned to the test subject with a time delay. Non-linear transformation may link data from different times to each other.

A device according to the invention is particularly suited to perform the method. Thus, in the spirit of the invention, these devices are routinely MEG or EEG online systems, which is to say systems in which the data is acquired, electrically isolated, processed, and forwarded to the test subject.

By using the powerful real-time data acquisition and signal processing unit, in combination with, or by way of expansion of, a commercially available computer, the required computing power is provided in order to calculate the feedback signals in real time based on the acquired data and output these again in order to stimulate the patient.

The invention will be described in further detail below with reference to two embodiments and to the attached figures.

DESCRIPTION OF THE PREFERRED EMBODIMENT

Figure 1:
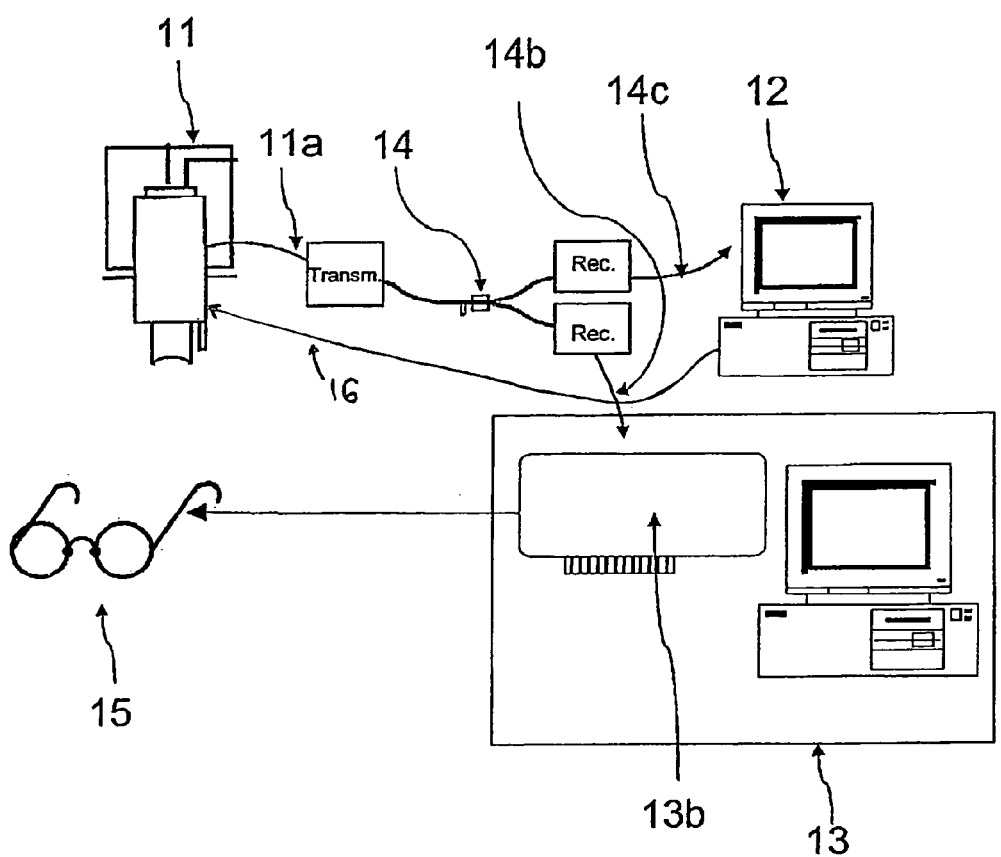
FIG. 1 is a schematic illustration of an MEG online system according to the invention.

At the top left of FIG. 1 is shown a multi-channel MEG 11 having a total of 148 individual channels, serving as a measuring system for acquisition of data. The multi-channel MEG 11 is typically directly connected to a workstation 12, as the first hardware component, via an optical fiber 11a and, for example, model Magnis 2500 WH, from 4D Neuroimaging, can be used. The workstation 12 has the function of storing the incoming data. In accordance with the state of the art, in the offline mode, the data is evaluated at a later time, after the data has been acquired by the measuring system.

In addition, the workstation 12 serves to control the measuring system 11, with respect to the measuring process thereof. To this end, another connecting line 16 is provided between the workstation 12 and the measuring system 11.

According to the invention, this commercially available measuring system 11 is connected via an optical fiber coupler 14 to a second hardware component 13 having a real-time data acquisition and signal processing unit 13b.

For this interference-free coupling to the existing MEG measuring system 11 with the workstation 12, the optical fiber coupler 14 is provided on the optical fiber 11a, which extends from the measuring system 11.

Figure 2:
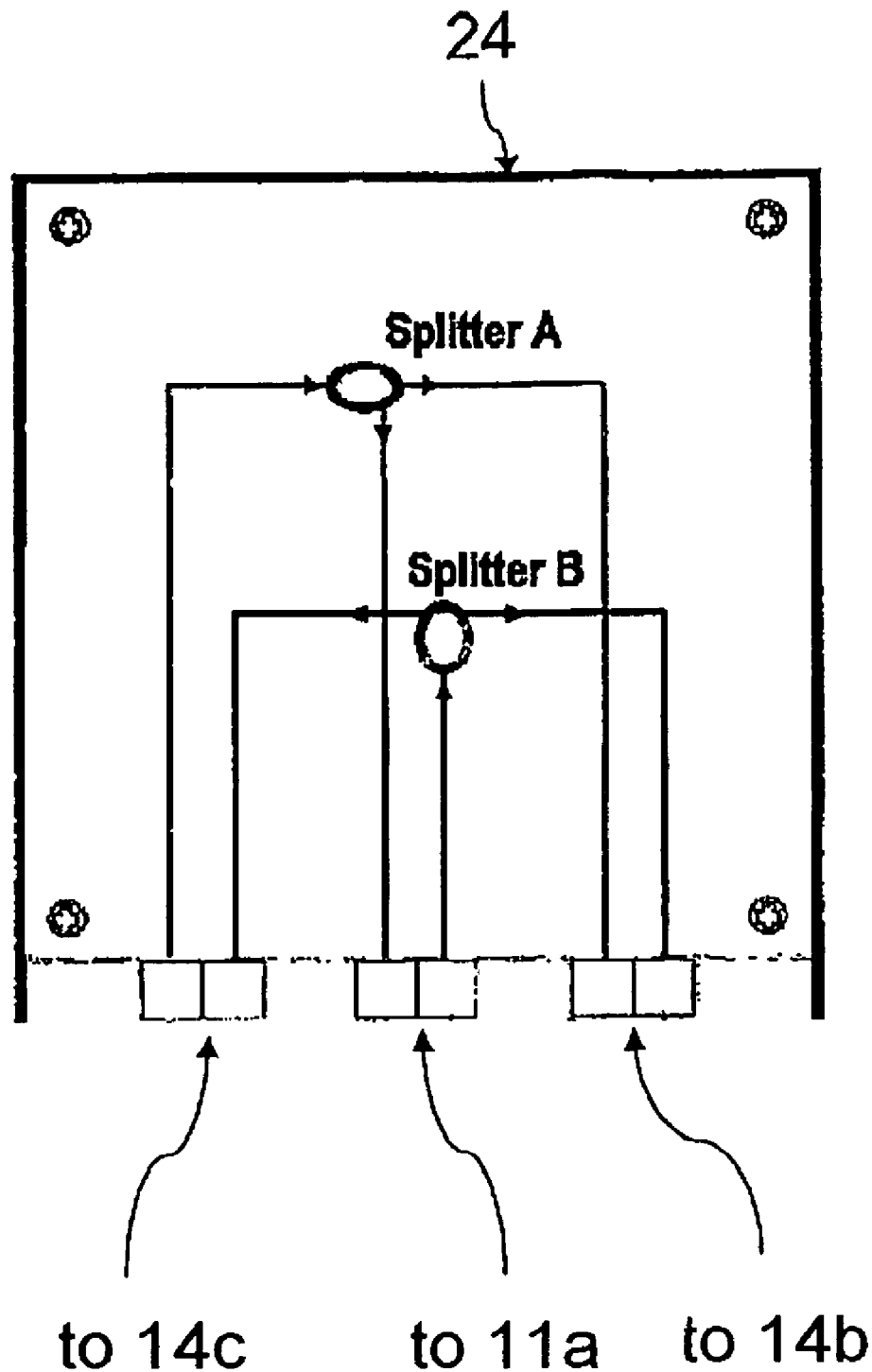
FIG. 2 is an optical fiber coupler as the means according to the invention for the electrical isolation of data and connections thereof.

FIG. 2 shows signal guidance in the optical fiber coupler 14, 24 and isolation of an incoming optical signal with respect to two outputs.

The optical fiber coupler 14, 24 used is the multimode coupler 1x2-G62, 5/125, from TEDIS.

The optical fiber coupler 14, 24 achieves passive, optical coupling of the optical fibers on the line 11a to the optical fibers on lines 14b and 14c. It comprises connections for the optical fiber 11a from the measuring system 11, and two connections for the optical fibers 14c and 14b, to the first hardware component 12, and to the second hardware component 13. As a result, the optical fiber coupler 14, 24 can be easily connected to the existing magnetoencephalograph by connecting the corresponding cables with plugs.

The optical fiber coupler 14, 24 achieves electrical isolation of the data stream coming from the MEG electronic sensor system (not shown) in the measuring system 11.

The optical fiber coupler 14, 24 divides the data stream from the measuring system 11, via the line 11a, into two identical and complete data sets on the two lines 14c and 14b. The data stream is thus copied into two unmodified data sets, which are identical to each other, and conducted to the two outputs on the optical fiber coupler 14, 24 in the form of optical signals.

Both of the hardware components 12 and 13 receive, without interference, a complete set of the data acquired from the test subject by the MEG measuring system 11. The line 14c leads to the workstation 12 in which the data is continuously recorded. Line 14b leads to the second hardware component 13 (bottom right, in FIG. 1), in which the data is processed in real time and forwarded to the test subject so as to generate stimulatory signals for the same.

Figure 3:
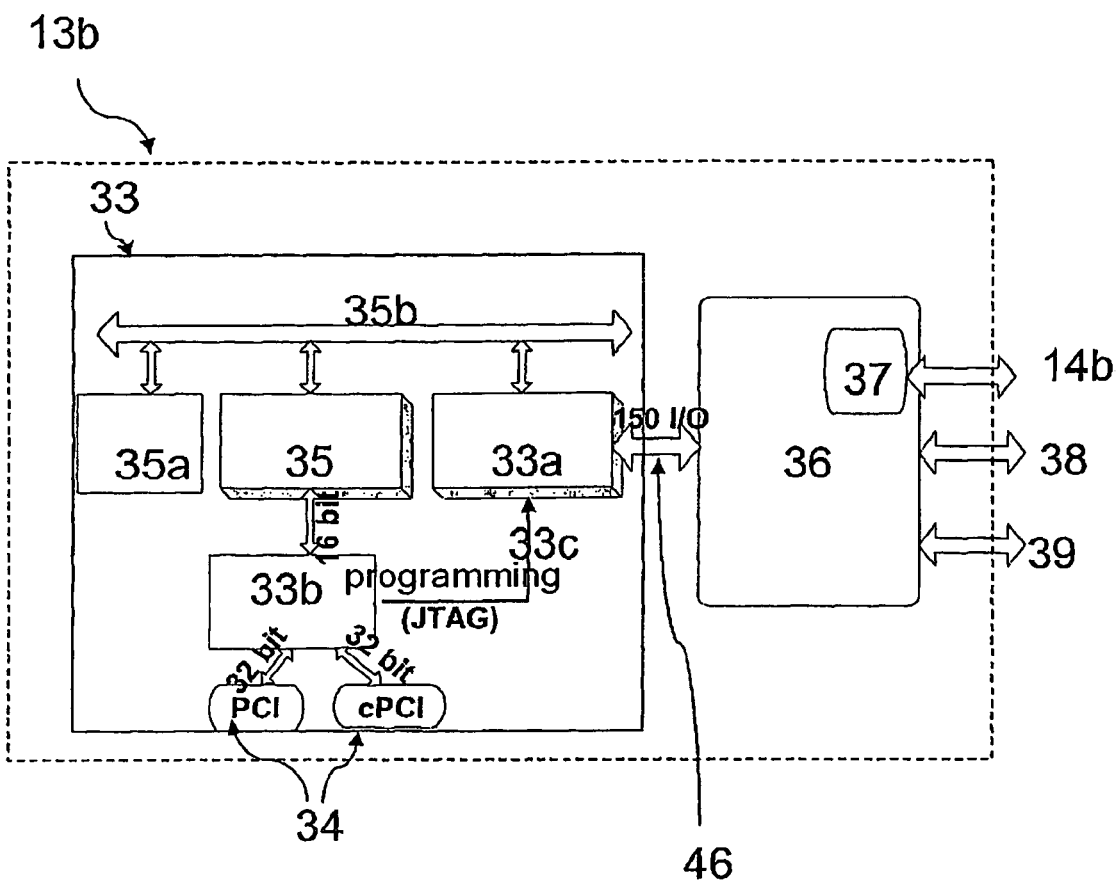
FIG. 3 is a circuit diagram of the PCI mainboard in the second hardware component comprising elements.

FIG. 3 shows a PCI mainboard 33, comprising individual components or elements according to the invention, in the form of a circuit diagram.

The second hardware component 13 for data processing in real time comprises a computer (see FIG. 1, bottom right). The computer has been expanded by a universal PCI mainboard 33. The mainboard 33 comprises, among other things, a field programmable gate array 33a (FPGA: Virtex XCV300) and a digital signal processor 35 (DSP D, module: Texas Instruments TMS320c6713). The PCI mainboard 33, in combination with the components thereof, constitutes the real-time data acquisition and processing unit 13b in the second hardware component 13. Real-time processing of the data measured by the measuring system 11 is important for the generation of feedback signals for the test subject.

The data acquisition and processing unit 13b (see FIG. 1) uses a PCI or compact PCI (cPCI) expansion bus 34 in the computer, so as to expand the same. The embodiment according to the invention as shown in FIG. 3 is based on a PCI mainboard 33. The board 33 establishes the connection between the PCI or cPCI bus 34 and the real-time processor unit 35, 35a, via a PCI controller 33b.

The processor unit 35, 35a comprises a module having a digital signal processor (DSP) 35 with sufficiently large RAM 35a, for example at least 16 MB. Via the local data bus 35b (32 bit data/addresses), the digital signal processor DSP 35 can exchange data with the element present on the PCI mainboard 33 using programmable hardware, the FPGA 33a.

The input and output components are provided on a separate daughterboard, which is the input and output module 36. The input and output module 36 has an optical fiber interface 37 to the optical fiber coupler 14, 24 (FIG. 1 and FIG. 2) of the magnetoencephalograph, as well as analog outputs 38 for stimulation of the test subject, and digital inputs and outputs for inputting and outputting time stamps, referred to as triggers 39. The hardware configuration of the field programmable gate array 33a allows for determination of the input and output behavior of the entire data acquisition and processing unit 13b, and this is configured via a JTAG interface 33c.

The field programmable gate array (FPGA) 33a internally provides a list of records, which can be written or read by addressing defined addresses.

The 32-bit floating point DSP TMS320c6713 is clocked at 225 MHz and can deliver a theoretical computing power of 1800 MIPS (million instructions) or 1350 MFLOPS (million floating point operations) per second.

On the computer in the second hardware component 13 for the MEG online system, the lead 14b is inserted into an optical fiber plug 37 (SC/PS duplex plug) of the real-time data acquisition unit 13b (see FIG. 1, bottom right). This completes all the connections to the MEG measuring system 11.

Figure 4:
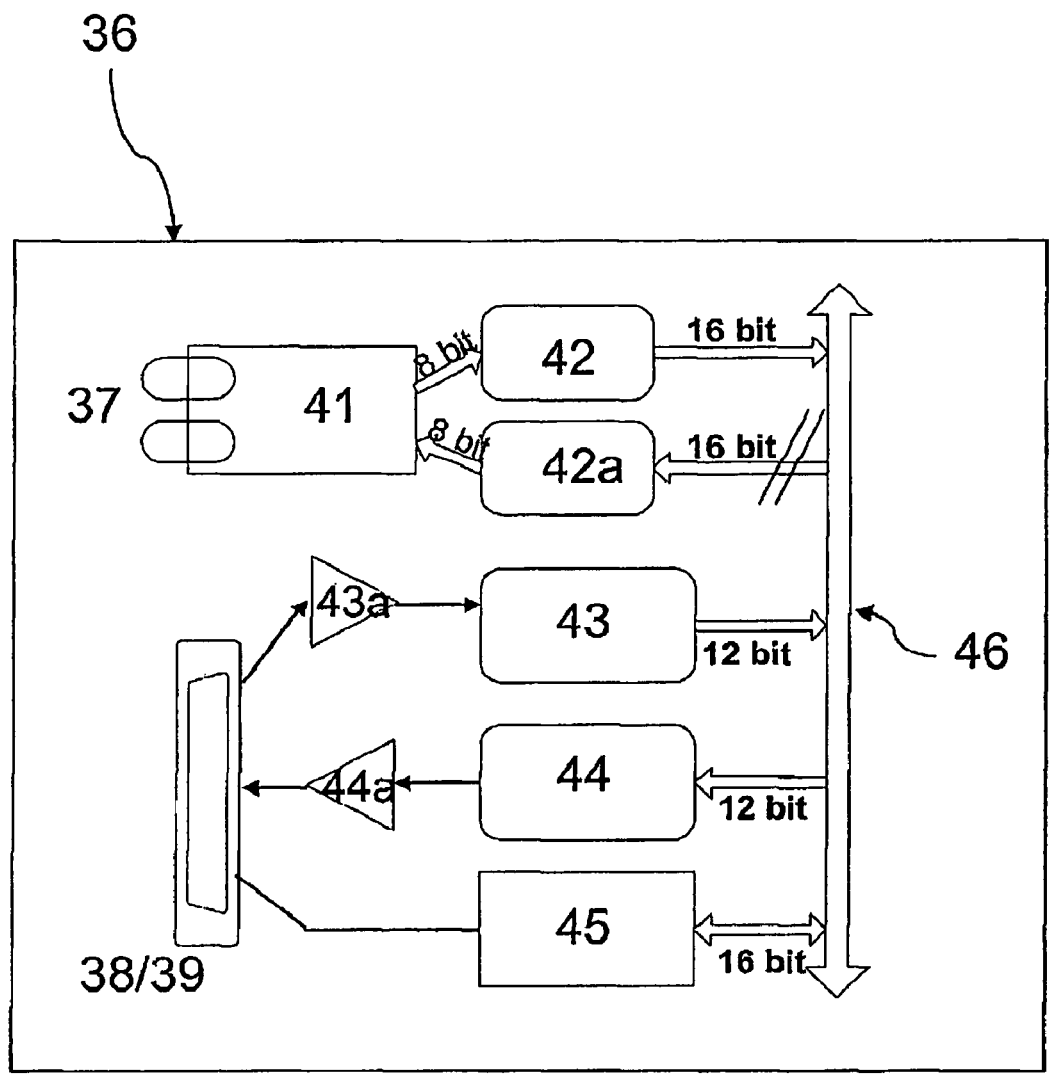
FIG. 4 is a circuit diagram of the input and output module of the PCI mainboard.

The input and output module 36 for the data acquisition and processing unit 13b is shown in FIG. 4.

The input and output module 36 comprises interfaces with the MEG measuring system 11. The data that arrives from the MEG measuring system 11 as light pulses is conducted via the optical fiber 14b to the plug 37 on the module 36. The module has a fiberoptic transceiver 41. The transceiver converts the optical signals into electric signals. The serial data stream is checked for errors by means of a hotlink receiver 42 and parallel data bytes are produced. The converted data is forwarded via the data bus 46 to the field programmable gate array (FPGA) 33a (see FIG. 3) for further processing. An existing hotlink transmitter 42a remains unused for data output. This is indicated by an interrupted data stream from the bus 46 to the hotlink transmitter 42a.

The input and output module 36 further comprises analog inputs, such as the plug 39, via which incoming data is conducted to an analog-to-digital converter 43 (4 channels, 12 bit ADC, +/−10 volt) via an amplifier 43a.

After digitization, the data is read via the data bus 46 by the FPGA 33 (see FIG. 3). The signals to be sent for stimulation purposes are written as electrical data via the bus 46 in the digital-to-analog converter 44 (4 channels, 12 bit DAC, +/−10 volt). The analog signals that are produced are output to the plug 38 for stimulation purposes following an amplification process in the amplifier 44a (see FIG. 3). The data is conducted via the plug 38 to a third hardware component 15 comprising optical goggles.

The digital inputs and outputs 45 (16 bit digital, input/output) are led to the plug 39 and used for outputting or reading time stamps (triggers). The data that arrives from the MEG measuring system 11 as light pulses is thus received by the photodetector in the optical fiber element 37 (FIG. 3) and converted into digital signals, which are conducted to the FPGA 33a. The data is pre-processed by the FPGA 33a using adjustable filters and forwarded to the digital signal processor 35 following suitable correction. In the digital signal processor 35, the data is processed in real time using suitable algorithms that are matched to the purpose of application for the test subject. Based on the calculations, data is provided for an output signal for stimulation purposes. This data is again written in the field programmable gate array (FPGA) 33a and reaches the analog output element 44 on the input and output module 36, via the bus 46. The signal is again amplified by the amplifier 44a and output as the stimulation signal via the plug 38.

The measured data and the calculated data continue to be transmitted, via the PCI controller 33b and the PCI bus 34, to the computer (not shown). The software implemented by the computer of the second hardware component displays the data or signals online, stores the information, and can perform additional evaluation. In this context, it should be emphasized that the workstation 11, as the first hardware component in the present example, only performs the function of controlling the measuring system for acquisition of the data.

For additional measuring tasks, such as the recording of a plurality of MEG channels, four analog inputs with 12 bit resolution are available. In addition, four analog outputs and 16 digital input and output channels are provided. The analog outputs are used to generate the analog feedback signals for stimulation experiments. As a result, it is possible to stimulate a test subject based on brain activities that are measured and processed in real time, using the method. In this way, the method according to the invention allows the processed data to be transformed in a linear or non-linear manner and returned to the test subject with a time delay. Non-linear transformation may link data from different times to each other.

During feedback, the test subject is supplied with data for stimulation purposes, wherein the data has been calculated from the currently measured data. To this end, the real-time capability of the data acquisition and processing unit 13b is used, with a new stimulation value being calculated at each scan time and output to a channel on the analog interface.

The feedback or stimulation signal is derived either from an MEG sensor, or from the power density curve of a region in the brain. Consequently, for these experiments, the power density curve of a brain area must be calculated for each scan point in real time. Then, the signal is bandwidth-limited, and the feedback signal is calculated. These calculations are performed in the digital signal processor (DSP) 35. A second embodiment relates to a device such as that in embodiment 1, but without the first hardware component, which is the workstation 12.

The real-time data acquisition and processing unit 13b also stores the data from the measuring system 11, in place of the workstation 12. In addition, the unit 13b processes the data in real time. The real-time data acquisition and processing unit 13b stores the acquired and processed data and additionally controls the measuring process of the measuring system 11 for acquisition of data. In this case, the device is provided with only one connecting line 11a, via which the real-time data acquisition and processing unit 13b receives signals from the measuring system 11 for acquisition of the data. Isolation of the data is no longer required since the tasks relating to the storage and processing of the data and to the control of the measuring system are assumed solely by the real-time data acquisition and processing unit 13b. The measuring system is controlled by the data acquisition and processing unit 13b via another line (not shown).

It is of course also possible in principle to use the second hardware component shown for calculations and data feedback for an EEG online system.

The invention claimed is:

1. A device for measuring biomedical data of a test subject, comprising:
   a measuring system for acquisition of the data, the measuring system coupled to a test subject and having multiple channels for detecting signals from the test subject, the detected signals comprising acquired data;
   a first hardware component for recording the data,
   a data acquisition and processing unit,
   at least one connecting line for transmitting the data from the measuring system to the first hardware component, and
   a device for electrical isolation of the data on the connecting line, between the measuring system for acquisition of the data and the first hardware component for recording the data,
   wherein the electrical isolation device passively couples an input line to each of a first output line and a second output line, the electrical isolation device providing electrical isolation among signals traversing the input line, the first output line and the second output line, respectively,
   wherein the input line connects the measuring system to the electrical isolation device and propagates the detected signals from the multiple channels of the measuring system;
   wherein the first hardware component comprises a first computing system, coupled to the measuring system, including memory for storing the acquired data and a processor for controlling acquisition of data by the measuring system;
   wherein the data acquisition and processing unit is distinct from the measuring system and the first computing system and generates feedback signals to stimulate either one or both of brain tissue and other tissue of the test subject;
   wherein the first output line connects the electrical isolation device to the first computing system and propagates the detected signals from the multiple channels of the measuring system from the electrical isolation device to the first computing system;
   wherein the second output line connects the electrical isolation device to the data acquisition and processing unit and propagates the data signals from the multiple channels of the measuring system from the electrical isolation device to the data acquisition and processing unit;

wherein a first connection path is formed between the measuring system and first computing system by the input line, electrical isolation device, and first output line;

wherein a second connection path is formed between the measuring system and the first computing system, distinct from and independent of the first connection path, and along which the first computing system sends control signals to the measuring system to control acquisition of data along the first connection path; and wherein the measuring system acquires data on an ongoing basis and the data acquisition and procession unit comprises a processing unit which processes currently acquired data in real time to generate in response said feedback signals for stimulating the test subject responsive to each acquisition of acquired data, said feedback signals being distinct from the control signals.

2. A device according to claim 1, in which the electrical isolation device comprises an optical fiber coupler or an electrical isolation amplifier as a passive means for isolating the detected signals propagating along the input line, first output line and second output line, respectively.

3. The device according to claim 1, wherein the data acquisition and processing unit comprises components disposed on a PCI mainboard.

4. A device according to claim 3, wherein the data acquisition and processing unit comprises a field programmable gate array.

5. A device according to claim 1, wherein the data acquisition and processing unit comprises a digital signal processor.

6. A device according to claim 1, further comprising an output component, which receives the feedback signals from the data acquisition and processing unit and forwards the feedback signals to stimulate the test subject.

7. The device according to claim 6, wherein the output component comprises stimulation goggles and/or a sound source.

8. The device according to claim 1, in which the measuring system and the first hardware component together comprise an electroencephalograph or magnetoencephalograph.

9. A method for real-time stimulation of a test subject using the device of claim 1, comprising the following steps:
 a) biomedical data of the test subject is acquired by a measuring system,
 b) the acquired data is electrically isolated by the measuring system and copied,
 c) a copy of the data is processed, and
 d) the processed data is forwarded to the test subject in real time.

10. The method according to the preceding claim 9, comprising repetition of steps a) to d).

11. A method according to any one of claim 9 or 10, wherein copies of each of the acquired data and the processed data are continuously saved.

12. A method according to any one of claim 9 or 10, wherein the data is transformed in a linear or non-linear manner and returned to the test subject with a time delay.

13. A device according to claim 3, wherein the data acquisition and processing unit comprises a digital signal processor.

14. A device according to claim 4, wherein the data acquisition and processing unit comprises a digital signal processor.

* * * * *